United States Patent [19]

Gehret et al.

[11] Patent Number: 4,559,357
[45] Date of Patent: Dec. 17, 1985

[54] INSECTICIDAL AND ACARICIDAL PHENYLHYDRAZONO- AND PHENYLHYDRAZINO-PYRROLIDINES

[75] Inventors: Jean-Claude Gehret, Aesch; Walter Traber, Reinach, both of Switzerland

[73] Assignee: Ciba-Geigy Corporation, Ardsley, N.Y.

[21] Appl. No.: 501,456

[22] Filed: Jun. 6, 1983

[30] Foreign Application Priority Data

Jun. 11, 1982 [CH] Switzerland .......................... 3639/82
Jun. 11, 1982 [CH] Switzerland .......................... 3641/82
Aug. 26, 1982 [CH] Switzerland .......................... 5079/82

[51] Int. Cl.[4] .................. A01N 43/36; C07D 207/14; C07D 207/22
[52] U.S. Cl. .................... 514/423; 548/530; 548/538; 548/540; 548/558; 514/426
[58] Field of Search ............... 548/530, 540, 538, 558; 424/274; 514/423, 426

[56] References Cited

U.S. PATENT DOCUMENTS 3,936,444  2/1976  Botta ................................ 548/558 X
4,213,773  7/1980  Wolf ................................ 546/223 X
4,331,680  5/1982  Giles et al. ...................... 548/538 X

FOREIGN PATENT DOCUMENTS 1957783  5/1971  Fed. Rep. of Germany ...... 548/558
3035822  4/1981  Fed. Rep. of Germany .

OTHER PUBLICATIONS

Prochazka, et al.; C.A. 98:53683e (1983).
Frohberger, et al.; C.A. 80:108405—B (1974).
Etienne, et al; C.A. 72:55133—n (1970).

*Primary Examiner*—Joseph Paul Brust
*Attorney, Agent, or Firm*—Edward McC. Roberts; Frederick H. Rabin

[57] ABSTRACT

Compounds of the formula

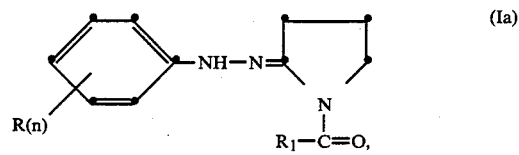

and of the isomeric formulae

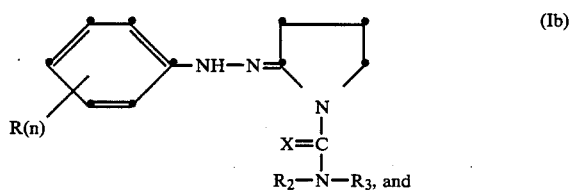

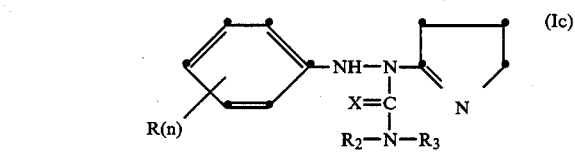

wherein R is alkyl or halogen, $R_1$ is hydrogen, optionally substituted alkyl or optionally substituted alkenyl, $R_2$ is hydrogen or methyl, $R_3$ is hydrogen, alkyl or alkenyl, and X is oxygen or sulfur, including their acid salts, are insecticidally and acaricidally active.

11 Claims, No Drawings

INSECTICIDAL AND ACARICIDAL PHENYLHYDRAZONO- AND PHENYLHYDRAZINO-PYRROLIDINES

The present invention relates to novel substituted phenylhydrazone and phenylhydrazine compounds, to processes for producing them, to compositions which contain these compounds as active components, and to the use of these compounds and compositions for controlling pests, particularly phytoparasitic and zooparasitic insects, and members of the order Acarina, including especially ectoparasites, for example mites and above all ticks.

In the German Offenlegungsschrift No. 3,035,822, phenylhydrazinepyrroline compounds are described and their use for controlling mites is suggested therein. These substances however can only partially satisfy the demands made of them in practice.

The novel compounds correspond to the general formula Ia

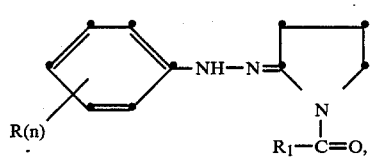

or, depending on the thermodynamic equilibrium, to the general formula Ib or to the general formula Ic

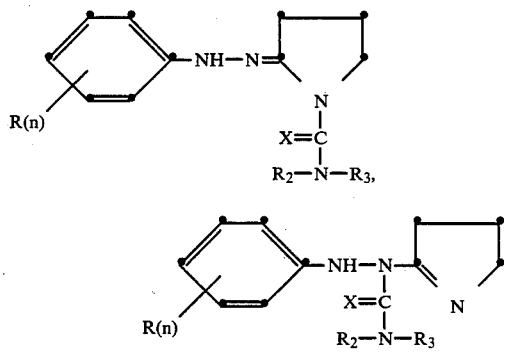

wherein
R is $C_1$–$C_4$-alkyl or halogen,
$R_1$ is hydrogen, $C_1$–$C_6$-alkyl which is unsubstituted or substituted by chlorine, fluorine or the carboxyl group, or it is $C_2$–$C_6$-alkenyl which is unsubstituted or substituted by chlorine, fluorine or the carboxyl group,
$R_2$ is hydrogen or methyl,
$R_3$ is hydrogen, $C_1$–$C_4$-alkyl or $C_2$–$C_4$-alkenyl,
X is oxygen or sulfur, and
n is zero or 1–5;
and also the salts thereof with inorganic or organic acids are embraced by the present invention.

Examples of inorganic acids are: hydrochloric acid, hydrobromic acid, hydriodic acid, sulfuric acid, phosphoric acid, phosphorus acid and nitric acid.

Examples of organic acids are: trifluoroacetic acid, trichloroacetic acid, oxalic acid, succinic acid, maleic acid, lactic acid, glycolic acid, aconitic acid, citric acid, benzoic acid, benzenesulfonic acid and methane-sulfonic acid.

Preferred compounds of the general formulae Ia, Ib and Ic are those wherein R is methyl and/or chlorine, and n is 1 or 2, and $R_1$, $R_2$, $R_3$ and X have the meanings defined under the formulae Ia, Ib and Ic. And preferred amongst these are those compounds of the formula Ia wherein R(n)=2,3-dichloro.

The alkyl groups denoted by R, $R_1$ and $R_3$ embrace methyl, ethyl and the isomers of propyl and of butyl, and in the case of $R_1$ also those of pentyl and of hexyl. The symbols $R_1$ and $R_3$ as alkenyl groups are ethenyl as well as the propenyls and the butenyls, and for $R_1$ additionally the pentenyls and hexenyls.

The alkyl and alkenyl groups can be straight-chain or branched-chain.

The compounds of the formula Ia can be produced by methods known per se (cp. Houben-Weyl, Vol. XI, Part 2, p. 3), for example as follows:

In the formulae II and III, the symbols have the following meanings: A is halogen, preferably chlorine, or the group —OC(O)$R_1$; and R, $R_1$ and n are as defined under the formula Ia.

The reaction is performed at temperatures of 0° to 100° C., preferably 10° to 50° C., in the presence of a solvent. Suitable solvents are for example: alkanes, ethers, chlorinated hydrocarbons, aromatic hydrocarbons, such as benzene, toluene or the xylenes; or organic bases, for example pyridine, triethylamine or N-methylpyrrolidone; or organic acids, such as acetic acid or chloroacetic acid.

The compounds of the formulae Ib and Ic can be produced, provided that $R_2$ is hydrogen, by methods known per se (cp. Houben-Weyl, Vol. VIII, p. 132 and p. 157), by reacting compounds of the formula IV with compounds of the formula IVa (isocyanates or isothiocyanates)

$R_3N=C=X$         (IVa), wherein R, $R_3$, X and n have the meanings defined for the formulae Ib and Ic.

The reaction proceeds between −30° and +100° C. in the presence of a solvent. To specifically produce compounds of the formula Ic, the temperature range chosen is between −30° and +40° C., preferably between −10° and +40° C. The temperature range taken for the production of compounds of the formula Ib is between +55° and +100° C., preferably between +60° and +80° C. In the transition range between +40° and +55° C., the two forms Ib and Ic are obtained, depending on the individual case (structure, reaction time), as a mixture.

Suitable solvents are for example: ethers, such as diethyl ether, tetrahydrofuran or dioxane, chlorinated hydrocarbons, such as dichloromethane, chloroform or carbon tetrachloride, aromatic substances, such as benzene, toluene or xylenes, as well as further inert solvents such as methyl ethyl ketone or actonitrile. Compounds of the formula Ic can be converted by a longish period of heating, preferably in a solvent, at 55° to 100° C., almost completely into the corresponding Ib compounds.

It is also possible to produce compounds of the formulae Ib and Ic, in a manner known per se, by reaction of compounds of the formula IV with a carbamoyl chloride of the formula IVb

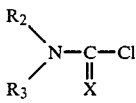

(IVb)

wherein R, $R_2$, $R_3$, X and n have the aforesaid meanings, $R_2$ and $R_3$ not being however hydrogen. The relevant information given above applies analogously to this reaction. The reaction temperature is −30° to +150° C. The reaction is carried out in the presence of one of the above-mentioned solvents, whereby the addition of an organic base, such as pyridine, triethylamine or N-methylpyrrolidone, which can also serve as sole solvent, is advantageous.

It is moreover possible to produce the compounds of the formulae Ib and Ic by reacting amines of the formula $R_2R_3NH$ with phosgene to the corresponding carbamoyl chlorides of the formula IVb, and then reacting these in situ with compounds of the formula IV, in which process the reaction temperatures and the reaction media used are in accordance with those of the last-mentioned method.

EXAMPLE 1

Production of 2-[N'-(2'-chloro-4'-methylphenylhydrazono)]-1-chloroazetyl-pyrrolidine 4.6 g of chloroacetic acid anhydride, dissolved in 40 ml of toluene, are slowly added dropwise at room temperature to 6.0 g (0.027 mol) of 2-[N'-(2'-chloro-4'-methylphenylhydrazono)]-pyrroline, dissolved in 80 ml of toluene. The occurring reaction proceeds slightly exothermically. The reaction mixture is then stirred for 20 hours at room temperature, and is subsequently concentrated in a rotary evaporator. After cooling, the residue is suspended in an ethyl acetate/diethyl ether mixture, and the precipitate is filtered off as white powder; yield: 3.2 g (=39% of theory); m.p. 134°–136° C.

EXAMPLE 2

Production of 2-[N'-(2',3'-dichlorophenylhydrazono)]-1-azetyl-pyrrolidine 8.2 g (0.08 mol) of acetic anhydride, dissolved in 20 ml of dichloromethane, are slowly added dropwise at room temperature to 17.0 g (0.07 mol) of 2-[N'-(2',3'-dichlorophenylhydrazino)]-pyrroline, dissolved in 100 ml of dichloromethane. The occurring reaction proceeds exothermically. The reaction mixture is then stirred for 20 hours at about 40° C., and subsequently extracted by shaking firstly with aqueous $NaHCO_3$ solution and afterwards with an NaCl solution. After drying of the organic phase, this is concentrated by evaporation, and the residue remaining is recrystallised from an ethyl acetate/diethyl ether mixture. The product is obtained in the form of white crystals; yield: 13.0 g (=65% of theory); m.p. 151°–153° C.

The following compounds of the formula Ia are produced in a manner analogous to that described in the above Examples.

TABLE I

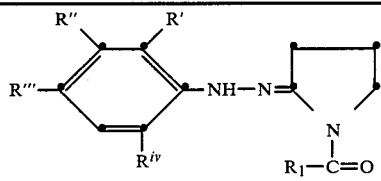

| No. | R' | R'' | R''' | $R^{iv}$ | $R_1$ | Physical data |
|---|---|---|---|---|---|---|
| 1 | Cl | H | $CH_3$ | H | $-CH_2Cl$ | m.p. 134–136° C. |
| 2 | Cl | Cl | H | H | $-CH_3$ | m.p. 150–152° C. |
| 3 | Cl | Cl | H | H | $-CH_2Cl$ | m.p. 149–151° C. |
| 4 | Cl | Cl | H | H | $-CF_3$ | m.p. 145–147° C. |
| 5 | Cl | Cl | H | H | $-C_2H_5$ | m.p. 138–139° C. |
| 6 | Cl | Cl | H | H | $-C_3H_7$ | m.p. 98–100° C. |
| 7 | Cl | Cl | H | H | $-CH(CH_3)_2$ | m.p. 151–153° C. |
| 8 | Cl | Cl | H | H | $-CH=CH-COOH$ | m.p. 188° C. (decomp.) |
| 9 | Cl | Cl | H | H | $-CH_2-CH_2-COOH$ | m.p. 176–177° C. |
| 10 | Cl | H | H | H | $-CH_3$ | m.p. 128–129° C. |
| 11 | H | Cl | H | H | $-CH_2Cl$ | m.p. 144–146° C. |
| 12 | Cl | H | Cl | H | $-C_3H_7$ | m.p. 130–132° C. |
| 13 | Cl | H | H | Cl | $-CH(CH_3)_2$ | $n_{24}^{D}$ 1,5637 |
| 14 | Cl | H | H | Cl | $-C_2H_5$ | m.p. 97–99° C. |
| 15 | $CH_3$ | Cl | H | H | $-CH_2Cl$ | m.p. 150–151° C. |
| 16 | Cl | H | $CH_3$ | H | $-CH(CH_3)_2$ | m.p. 109–113° C. |
| 17 | Cl | Cl | H | H | H | m.p. 146–148° C. |

TABLE I-continued

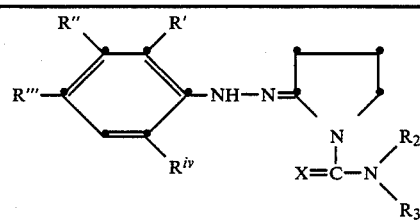

| No. | R' | R'' | R''' | R$^{iv}$ | R$_1$ | Physical data |
|---|---|---|---|---|---|---|
| 18 | Cl | Cl | H | H | n-C$_5$H$_{11}$ | |
| 19 | —CH$_3$ | —CH$_3$ | H | H | —CH$_2$Cl | |
| 20 | —CH$_3$ | —CH$_3$ | H | H | —C$_2$H$_5$ | |
| 21 | —CH$_3$ | H | Cl | H | —CH$_3$ | |
| 22 | —CH$_3$ | H | Cl | H | —CH$_2$Cl | |
| 23 | —CH$_3$ | H | Cl | H | i-C$_3$H$_7$ | |
| 24 | —CH$_3$ | H | Cl | H | n-C$_6$H$_{13}$ | |
| 25 | —CH$_3$ | H | —CH$_3$ | H | —CH$_3$ | |
| 26 | —CH$_3$ | H | —CH$_3$ | H | —CH$_2$Cl | |
| 27 | —CH$_3$ | H | —CH$_3$ | H | n-C$_3$H$_7$ | |
| 28 | Cl | Cl | H | H | n-C$_4$H$_9$ | m.p. 100–101° C. |
| 29 | H | Cl | Cl | H | —CH$_3$ | m.p. 185–190° C. |

EXAMPLE 3

Production of 2-[N'-(2,3-dichlorophenylhydrazono)]-1-methylthiocarbamoyl-pyrrolidine 2.75 g (0.037 mol) of methylisocyanate, dissolved in 60 ml of toluene, are added dropwise at 60° C. in an N$_2$ atmosphere to a solution of 6.1 g (0.025 mol) of 2-[N'-(2,3-dichlorophenylhydrazino)]-pyrroline, dissolved in 80 ml of toluene, in the course of 1 hour, and the mixture is stirred at this temperature for 20 hours. After cooling in an ice-bath, 4 g of final product (50% of theory) crystallise and are washed with diethyl ether; m.p. 181°–182° C. (compound No. 2/II).

EXAMPLE 4

Production of compound No. 2/II by thermal conversion of compound No. 2/III 0.5 g of the compound No. 2/III is dissolved in 30 ml of toluene, and the solution is heated, with gentle stirring, for 24 hours at 57°–60° C. The solution is afterwards concentrated by evaporation, and the residue is chromatographed through silica gel with methylene chloride as the eluant. The yield is 0.47 g of the compound No. 2/II; m.p. 180°–182° C.

The following compounds are produced in a manner analogous to that described in the above Examples 3 and 4, or by one of the processes mentioned in the foregoing.

TABLE II

| No. | R' | R'' | R''' | R$^{iv}$ | R$_2$ | R$_3$ | X | Physical data [m.p. in °C.] |
|---|---|---|---|---|---|---|---|---|
| 1 | Cl | Cl | H | H | H | —CH$_3$ | O | 148–150 |
| 2 | Cl | Cl | H | H | H | —CH$_3$ | S | 180–182 |
| 3 | Cl | Cl | H | H | H | —CH(CH$_3$)$_2$ | O | 140–150 (dec.) |
| 4 | Cl | Cl | H | H | H | —CH$_2$—CH=CH$_2$ | O | 110–111 |
| 5 | Cl | H | H | H | —CH$_3$ | H | O | |
| 6 | Cl | H | H | H | H | —CH$_2$CH=CH$_2$ | S | |
| 7 | Cl | H | H | H | —CH$_3$ | H | S | |
| 8 | H | Cl | H | H | H | —CH$_2$CH=CH$_2$ | O | 116–118 |
| 9 | Cl | H | Cl | H | H | —CH$_2$CH=CH$_2$ | O | |
| 10 | Cl | H | H | Cl | H | —CH$_3$ | S | |
| 11 | Cl | H | H | Cl | H | n-C$_4$H$_9$ | O | |
| 12 | Cl | H | Cl | Cl | —CH$_3$ | H | O | |
| 13 | Cl | H | —CH$_3$ | H | H | —CH(CH$_3$)$_2$ | O | 109–113 |
| 14 | —CH$_3$ | Cl | H | H | H | —C$_2$H$_5$ | O | |
| 15 | Cl | Cl | H | H | H | n-C$_4$H$_9$ | O | 55–56 |
| 16 | Cl | Cl | H | H | H | —CH$_2$CH=CH$_2$ | S | 140–141 |
| 17 | —CH$_3$ | Cl | H | H | H | —CH$_2$CH=CH$_2$ | S | |
| 18 | —CH$_3$ | H | Cl | H | —CH$_3$ | H | S | |
| 19 | Cl | Cl | H | H | —CH$_3$ | —CH$_3$ | O | 97–99 |
| 20 | Cl | Cl | H | H | —CH$_3$ | —CH$_3$ | S | |
| 21 | Cl | —CH$_3$ | H | H | —CH$_3$ | —CH$_3$ | O | |
| 22 | Cl | —CH$_3$ | H | H | —CH$_3$ | —CH$_3$ | S | |

TABLE II-continued

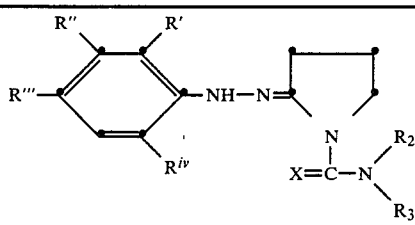

| No. | R' | R" | R''' | $R^{iv}$ | $R_2$ | $R_3$ | X | Physical data [m.p. in °C.] |
|---|---|---|---|---|---|---|---|---|
| 23 | Cl | H | Cl | H | H | i-$C_3H_7$ | O | |
| 24 | Cl | Cl | H | H | H | n-$C_4H_9$ | S | 136-138 |
| 25 | H | Cl | Cl | H | H | —$CH_3$ | S | 171-172 |
| 26 | H | Cl | Cl | H | H | —$CH_3$ | O | 190-192 |

EXAMPLE 5

Production of 2-[N'-(2,3-dichlorophenyl)-N-(isopropylcarbamoyl)-hydrazino]-pyrroline To 7.3 g (0.03 mol) of 2-[N'-(2,3-dichlorophenyl-hydrazino)]-1-pyrroline, dissolved in 100 ml of methylene chloride, are added dropwise at 0° to 5° C. 2,8 g (0.033 mol) of isopropylisocyanate, dissolved in 10 ml of methylene chloride. The reaction mixture is then stirred at about 5° C. for a further 1 hour. The solvent is subsequently evaporated off in vacuo, and the white residue remaining is suspended in about 30 ml of absolute diethyl ether and filtered. There is obtained on drying a white powder; yield: 8.5 g (86% of theory); m.p.: 109°-111° C. (compound No. 3/III).

The following compounds are produced in a manner analogous to that described in the above Example.

TABLE III

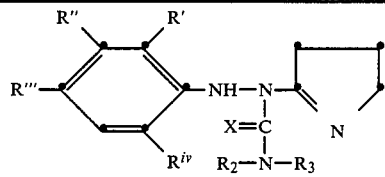

| No. | R' | R" | R''' | $R^{iv}$ | $R_2$ | $R_3$ | X | Physical data [m.p. in °C.] |
|---|---|---|---|---|---|---|---|---|
| 1 | Cl | Cl | H | H | H | —$CH_3$ | O | 109-110 |
| 2 | Cl | Cl | H | H | H | —$CH_3$ | S | 100-101 |
| 3 | Cl | Cl | H | H | H | —$CH(CH_3)_2$ | O | 109-111 |
| 4 | Cl | Cl | H | H | H | —$CH_2$—$CH=CH_2$ | O | 122-123 |
| 5 | Cl | H | H | H | —$CH_3$ | H | O | 97-99 |
| 6 | Cl | H | H | H | H | —$CH_2CH=CH_2$ | S | 96-97 |
| 7 | Cl | H | H | H | —$CH_3$ | H | S | 112-114 |
| 8 | H | Cl | H | H | H | —$CH_2CH=CH_2$ | O | 116-118 |
| 9 | Cl | H | Cl | H | H | —$CH_2CH=CH_2$ | O | 98-99 |
| 10 | Cl | H | H | Cl | H | —$CH_3$ | S | 117-120 |
| 11 | Cl | H | H | Cl | H | n-$C_4H_9$ | O | 94-96 |
| 12 | Cl | H | Cl | Cl | —$CH_3$ | H | O | 119-121 |
| 13 | Cl | H | —$CH_3$ | H | H | —$CH(CH_3)_2$ | O | 102-104 |
| 14 | —$CH_3$ | Cl | H | H | H | —$C_2H_5$ | O | 117-118 |
| 15 | Cl | Cl | H | H | H | n-$C_4H_9$ | O | 100-101 |
| 16 | Cl | Cl | H | H | H | —$CH_2CH=CH_2$ | S | 83-84 |
| 17 | —$CH_3$ | Cl | H | H | H | —$CH_2CH=CH_2$ | S | |
| 18 | —$CH_3$ | H | Cl | H | —$CH_3$ | H | S | |
| 19 | Cl | Cl | H | H | —$CH_3$ | —$CH_3$ | O | 83-88 |
| 20 | Cl | Cl | H | H | —$CH_3$ | —$CH_3$ | S | |
| 21 | Cl | —$CH_3$ | H | H | —$CH_3$ | —$CH_3$ | O | |
| 22 | Cl | —$CH_3$ | H | H | H | —$CH_3$ | S | |
| 23 | Cl | H | Cl | H | H | i-$C_3H_7$ | O | |
| 24 | Cl | Cl | H | H | H | n-$C_4H_9$ | S | 67-68 |
| 25 | H | Cl | Cl | H | H | —$CH_3$ | S | 94-95 |
| 26 | H | Cl | Cl | H | H | —$CH_3$ | O | 126-128 |

The compounds of the formulae Ia, Ib and Ic according to the invention and the compositions containing them as active component are distinguished in pest control by a particularly good biological activity and a favourable range of action. Furthermore, they have an unexpectedly high level of stability. The following compounds of the formula Ia prove to be particularly suitable for controlling pests:

2-[N'-(2',3'-dichlorophenyl-hydrazono)]-1-n-butyryl-pyrrolidine;

2-[N'-(2',3'-dichlorophenyl-hydrazono)]-1-chloroacetylpyrrolidine.

The activity of the active substances is directed against insects, and members of the order Acarina, in particular against ticks (Ixodidae), and of these especially against the species Rhipicephalus, Amblyomma and Boophilus; and also against mites, for example *Dermanyssus gallinae*. The spectrum of activity of the compounds according to the invention embraces all development stages, as well as the oviposition of fertile eggs. The effectiveness of the compounds of the formula I according to the invention is directed also against further ectoparasites, such as members of the orders Aphaniptera (for example blood-sucking fleas) and Phthiraptera (for example blood-sucking lice).

The increased stability of the compounds of the formulae Ia, Ib and Ic according to the invention ensures a duration of action which, in terms of time, covers the development cycles of several generations of parasites, so that, depending on the form of application, for example on productive animals, a single treatment per season is sufficient.

EXAMPLE 6

Test to determine action against ticks: mortality rate at various stages of development The test objects used are larvae (in each case about 50) and nymphs (in each case about 25) of the tick species *Amblyomma hebraeum* and *Boophilus microplus*, respectively. The test organisms are immersed for a short time in aqueous emulsions or solutions of the salts of the substances to be tested at a specific concentration. The emulsions or solutions in small test tubes are absorbed with cotton wool and the wetted test insects are then left in the contaminated test tubes. An evaluation with respect to larvae is made after 3 days, and with respect to nymphs and imagines after 14 days. There is determined the minimum substance concentration which results in a 100% mortality rate, expressed in ppm of active substance relative to the total amount of emulsion or solution.

Active substances from the Tables I–III are effective in the following concentration ranges:
 larvae: >0.1–10 ppm
 nymphs: >1–10 ppm.

EXAMPLE 7

Test to determine action against ticks: inhibition of oviposition

The test insects used are females of the cattle tick *Boophilus microplus* which have sucked themselves full. There are treated per concentration 10 ticks of an OP-resistant strain (for example Biarra strain) and 10 ticks of a normally sensitive strain (for example Weerongpilly strain). The ticks are fixed on plates covered with double adhesive tape, and are then either wetted with aqueous emulsions or with solution of the salts of the compounds to be tested, or brought into contact with a cotton-wool pad soaked with these liquids. and are subsequentially kept in an air-conditioned chamber under constant conditions. An evaluation is made after three weeks, and the overall inhibition of the oviposition of fertile eggs is determined.

The inhibitory effect of the substances is expressed in terms of the minimum substance concentration in ppm to produce a 100% effect against normally sensitive adult female ticks and resistant adult female ticks, respectively. Active substances listed in Tables I–III are fully effective in the concentration range of >16–125 ppm.

EXAMPLE 8

Test on phytoparasitic insects

Cotton plants are sprayed with test solutions containing 50 and 100 ppm, respectively of the compound to be tested.

After the drying of the moist coating, Spodoptera littoralis larvae ($L_3$) are settled onto the cotton plants. The test is carried out at 24° C. with 60% relative humidity.

Active substances listed in the Tables I–III exhibit the following stomach-poison action against Spodoptera larvae:

70–100% mortality rate at 50 or 100 ppm active substance concentration.

Results similar to those given in the above Examples 6 to 8 can be obtained with active substances from the Tables I–III also with a more prolonged period of application under practical conditions without having to carry out additional pH-value adjustments to stabilise the forms of application used in practice.

For the control of pests, the compounds of the formulae Ia, Ib and Ic according to the invention are used either on their own or in the form of compositions which also contain suitable carriers or additives or mixtures of such substances. Suitable carriers and formulation auxiliaries can be solid or liquid and they correspond to the substances commonly used in formulation practice, such as natural or regenerated substances, solvents, dispersing agents, wetting agents, adhesives, thickeners or binders.

For application, the compounds of the formulae Ia, Ib and Ic can be processed into the form of dusts, emulsion concentrates, granulates, dispersions, sprays, solutions or suspensions, the formulation of these preparations being effected in a manner which is common knowledge in the art.

The compositions according to the invention are produced in a manner known per se by the intimate mixing and/or grinding of active substances of the formulae Ia, Ib and Ic with suitable carriers, optionally with the addition of dispersing agents and solvents which are inert to the active substances. The active substances can be obtained and used in the following forms:

solid preparations: dusts, scattering agents, granules (coated, impregnated and homogeneous granules);
 liquid preparations:
  (a) water-dispersible concentrates of active substance: wettable powders, pastes or emulsions;
  (b) solutions: "pour-on" or sprays.

The content of active substance in the above described compositions is preferably between 0.1 and 95.0% by weight.

EXAMPLE 9

Emulsion concentrate 20 parts by weight of active substance are dissolved in 70 parts by weight of xylene, and to this solution are added 10 parts by weight of an emulsifier consisting of a mixture of an arylphenyl polyglycol ether and the calcium salt of dodecylbenzenesulfonic acid.

Water can be added in any proportion to the emulsion concentrate to form a milky emulsion.

EXAMPLE 10

Emulsion concentrate 5 to a maximum of 30 parts by weight of active-substance are dissolved at room temperature, with stirring, in 30 parts by weight of dibutyl phthalate, 10 parts by weight of solvent (low-viscous, highly aromatic petroleum distillate), and 15 to 35 parts by weight of Dutrex 238 FC (viscous highly aromatic petroleum distillate), and to this solution are added 10 parts by weight of an emulsifier mixture consisting of castor oil polyglycol ether and the calcium salt of dodecylbenzenesulfonic acid.

Milky emulsions are formed by adding water to the emulsion concentrate obtained.

EXAMPLE 11

Wettable powder 5 to 30 parts by weight of active substance are vigorously mixed, in a mixing apparatus, with 5 parts by weight of an absorbent carrier (silicic acid K 320 or Wessalon S), and 55 to 80 parts by weight of a carrier (*bolus alba* or kaolin B 24), and a dispersing agent mixture consisting of 5 parts by weight of a sodium lauryl sulfonate, and 5 parts by weight of an alkyl-aryl-polyglycol ether.

This mixture is ground in a dowelled disk mill or air jet mill to a particle size of 5–15 μm. The wettable powder thus obtained gives a good suspension in water.

EXAMPLE 12

Dust 5 parts by weight of finely ground active substance are thoroughly mixed with 2 parts by weight of a precipitated silicic acid, and 93 parts by weight of talcum.

EXAMPLE 13

| Pour-on solution | |
|---|---|
| active substance | 30.0 g |
| sodium dioctylsulfosuccinate | 3.0 g |
| benzyl alcohol | 48.0 g |
| peanut oil | 19.8 g |
| | 100.8 g = 100 ml. |

The active substance is dissolved with stirring in the benzyl alcohol, if necessary also with slight heating. To the solution are then added the sodium dioctyl sulfosuccinate and the peanut oil, and these are dissolved with heating and thorough stirring.

EXAMPLE 14

| Pour-on solution | |
|---|---|
| active substance | 30.00 g |
| sodium dioctylsulfosuccinate | 3.00 g |
| benzyl alcohol | 35.46 g |
| ethylene glycol monomethyl ether | 35.46 g |
| | 103.92 g = 100 ml. |

The active substance is dissolved, with vigorous stirring, in the major part of the mixture of the two solvents. The sodium dioctylsulfosuccinate is subsequently added and dissolved, if necessary with heating, and the mixture is then made up with the remaining part of the solvent mixture.

What is claimed is:

1. A substituted phenylhydrazone or phenylhydrazine compound of the formula Ia

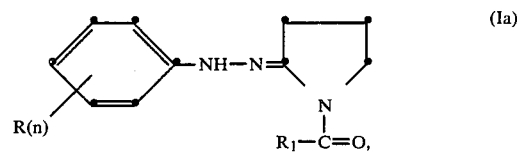

or of the formula Ib or Ic

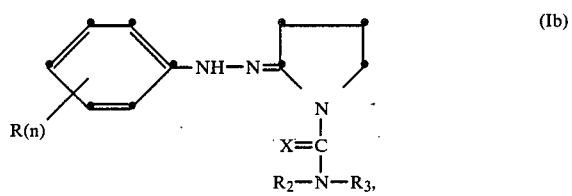

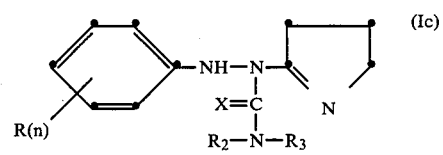

wherein

R is $C_1$–$C_4$-alkyl or halogen, $R_1$ is hydrogen, $C_1$–$C_6$-alkyl which is unsubstituted or substituted by chlorine, fluorine or the carboxyl group, or it is $C_2$–$C_6$-alkenyl which is unsubstituted or substituted by chlorine, fluorine or the carboxyl group, $R_2$ is hydrogen or methyl, $R_3$ is hydrogen, $C_1$–$C_4$-alkyl or $C_2$–$C_4$-alkenyl, X is oxygen or sulfur, and n is zero or 1–5, including the salts thereof with inorganic or organic acids.

2. A compound of the formula Ia, Ib or Ic according to claim 1, wherein R is methyl or chlorine, and n is 1 or 2.

3. A compound of the formula Ia according to claim 2, wherein R(n) is 2,3-dichloro.

4. A compound: 2-[N'-(2',3'-dichlorophenylhydrazono)]-1-n-butyryl-pyrrolidine according to claim 3.

5. A compound: 2-[N'-(2',3'-dichlorophenylhydrazono)]-1-chloroacetyl-pyrrolidine according to claim 3.

6. An insecticidal and acaricidal composition which contains as active ingredient an insecticidally or acaricidally effective amount of at least 1 compound of the formula Ia, Ib or Ic according to claim 1, together with an inert carrier.

7. A composition according to claim 6, which contains as active ingredient at least one compound of the formula

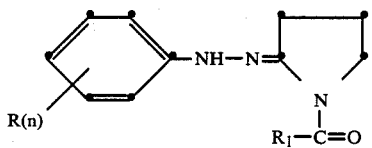

wherein
R(n) is 2,3-dichloro, and
$R_1$ is hydrogen, $C_1$–$C_6$-alkyl which is unsubstituted or substituted by chlorine, fluorine or the carboxyl group, or $C_2$–$C_6$-alkenyl which is unsubstituted or substituted by chlorine, fluorine or the carboxyl group.

8. A composition according to claim 7, which contains, as active ingredient, 2-[N'-(2',3'-dichlorophenyl-hydrazono)]-1-n-butyryl-pyrrolidine or 2-[N'-(2',3'-dichlorophenyl-hydrazono)]-1-chloroacetyl-pyrrolidine.

9. A method for controlling insects and acarids which comprises applying thereto or to the habitat thereof an insecticidally or acaricidally effective amount of a compound of the formula Ia, Ib or Ic according to claim 1.

10. A method according to claim 9 in which the compound is 2-[N'-(2',3'-dichlorophenyl-hydrazono)]-1-n-butyryl-pyrrolidine or 2-[N'-(2',3'-dichlorophenyl-hydrazono)]-1-chloroacetyl-pyrrolidine.

11. A method according to claim 9 in which the compound is of the formula

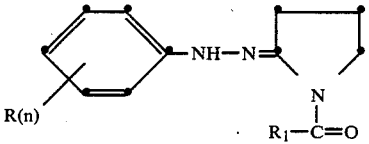

wherein
R(n) is 2,3-dichloro, and
$R_1$ is hydrogen, $C_1$–$C_6$-alkyl optionally substituted by chlorine, fluorine or the carboxyl group, or $C_2$–$C_6$-alkenyl optionally substituted by chlorine, fluorine or the carboxyl group.

* * * * *